(12) United States Patent
Kapoor

(10) Patent No.: US 8,498,685 B2
(45) Date of Patent: Jul. 30, 2013

(54) TOUCH SCREEN MEDICAL DIAGNOSTIC DEVICE AND METHODS

(75) Inventor: Trishul Kapoor, San Jose, CA (US)

(73) Assignee: Bionys, LLC., San Jose, CA (US)

( * ) Notice: Subject to any disclaimer, the term of this patent is extended or adjusted under 35 U.S.C. 154(b) by 317 days.

(21) Appl. No.: 12/929,318

(22) Filed: Jan. 14, 2011

(65) Prior Publication Data

US 2012/0184833 A1    Jul. 19, 2012

(51) Int. Cl.
*A61B 5/05* (2006.01)

(52) U.S. Cl.
USPC .............................. 600/346; 345/174; 348/77

(58) Field of Classification Search
USPC ................................ 600/346; 348/77; 345/174
See application file for complete search history.

(56) References Cited

U.S. PATENT DOCUMENTS

2011/0256024 A1* 10/2011 Cole et al. ..................... 422/68.1
2012/0029928 A1* 2/2012 Kountotsis ..................... 705/1.1

\* cited by examiner

*Primary Examiner* — Max Hindenburg
*Assistant Examiner* — Renee Danega
(74) *Attorney, Agent, or Firm* — Firasat Ali; William Nixon; Creso legal

(57) ABSTRACT

A capacitive touch screen device forms a capacitance between a body part of a user and a sensor layer. The sensor layer of the device includes capacitive sensors that allow a current to flow to the body part from the device when contact is made. The body part contacts the device through a bodily fluid. The current drawn is measured and a value for the bodily fluid is determined. This value is compared against known values to diagnose a possible medical condition or to infer characteristics of the bodily fluid.

18 Claims, 4 Drawing Sheets

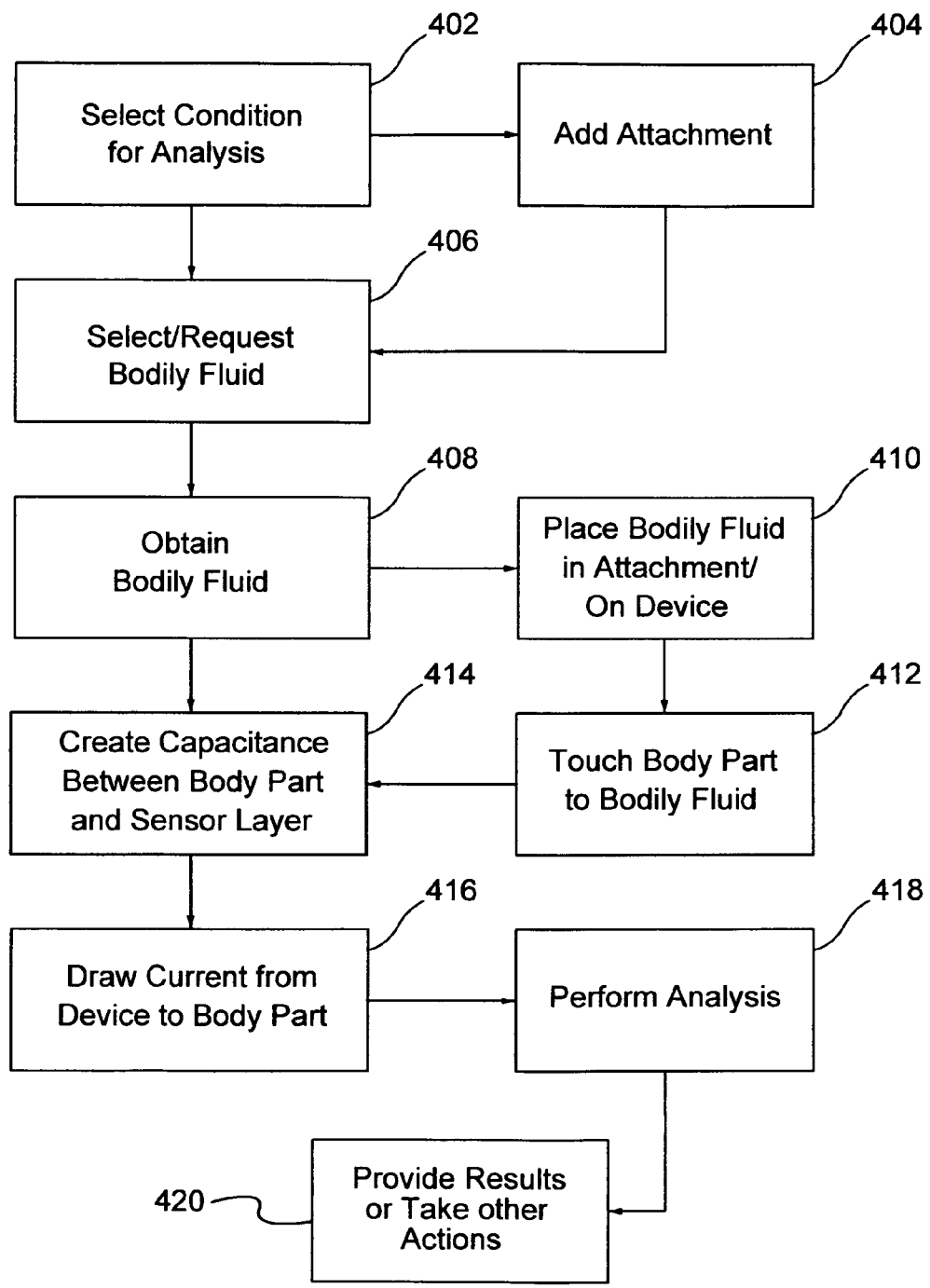

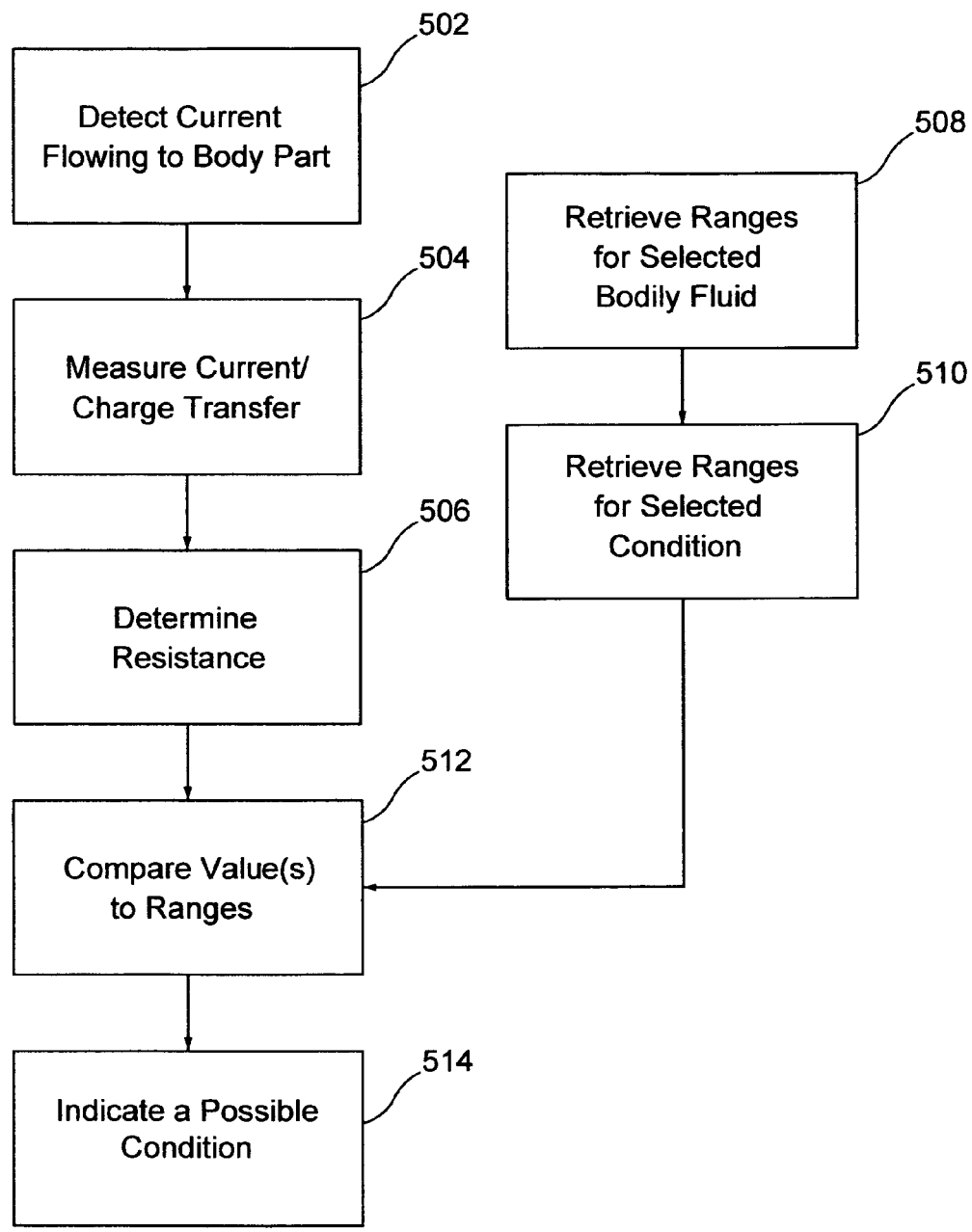

TOUCH SCREEN MEDICAL DIAGNOSTIC DEVICE AND METHODS

FIELD OF THE INVENTION

The present invention relates to a touch screen apparatus to detect possible medical conditions of a user. More particularly, the present invention relates to detecting medical conditions and alerts of the user by determining conductive properties to infer characteristics of a bodily fluid using the touch screen apparatus and associated methods.

DISCUSSION OF THE RELATED ART

Cystic fibrosis is a disease that causes thick, sticky mucus to accumulate in the lungs and digestive tract. Cystic fibrosis affects children and young adults and results in early death. Thus, early detection and treatment of the disease increases the chance of survival in this group. Preferably, the tests should be noninvasive and easy to administer.

A common test for cystic fibrosis is the sweat test, which determines the concentration of sodium chloride in sweat. Individuals suffering from cystic fibrosis have a high sodium chloride concentration in their body fluids. Conventional sweat tests may not be accurate with regard to infants and small children as these individuals do not sweat as much as adults or teenagers.

The sweat test also suffers from unreliability due to faulty execution. Inadequate sealing of the absorbent pad to the skin or a delay in transferring the pad to the weighing bottle may evaporate the water on the pad. The lack of water on the pad may lead to a higher concentration of sodium chloride in the test results. The longer the collection period for the sweat test, then the greater chance of evaporation. Moreover, results are not provided in a timely manner, and may take as long as 45 minutes to an hour.

Thus, though these techniques help in detecting cystic fibrosis, they suffer from possible misreading or a long wait for the results. The tests also are not convenient or conducive for data storage or records retention.

SUMMARY OF THE INVENTION

The present invention allows for a measurement that aids in the diagnosis of illnesses and medical conditions through an analysis of an amount of a bodily fluid, such as sweat, blood, saliva, and the like using a touch screen. For example, an amount of sweat may be used when one touches the screen. Using this example, the amount of sweat is analyzed for concentrations of sodium chloride, which indicates the probability of cystic fibrosis. A higher concentration of sodium chloride means a higher probability of that disease. Other conditions may be diagnosed using the altered conductance of the bodily fluid.

Bodily fluids contain variable concentrations of electrolytes. Electrolytes are ions that conduct electrically. Using electrolytes, humans can conduct electricity. When using a touch screen, an amount of current flows from the screen to the user from the device. Using this value, the present invention may determine the resistance of an amount of bodily fluid to identify possible conditions. The resistance of the bodily fluid may indicate conductivity of the bodily fluid as well, as conductivity is considered the inverse of resistivity. In short, bodily fluid resistance may be used to determine conductivity, which indicates illnesses or other medical conditions without invasive techniques. Other values instead of resistance may be used, such as conductivity or impedance. For simplicity, however, resistance is disclosed below.

According to the present invention, a method for determining a possible medical condition using a touch screen device is disclosed. The method includes placing a bodily fluid on a layer of the device. The method also includes contacting a body part with the bodily fluid. The method also includes drawing a current from the device to the body part through the bodily fluid. The method also includes performing an analysis on the bodily fluid based on a measurement corresponding to the current drawn from the device. The method also includes indicating whether a probability for a medical condition exists based on the analysis.

Further according to the present invention, a method for determining a potential medical condition using a touch screen device is disclosed. The method includes drawing a current from the device to a body part of a user through a bodily fluid. The method also includes determining a value for the bodily fluid based on the current. The method also includes comparing the value to a range of values corresponding to a medical condition. The method also includes providing a result to the user regarding the medical condition.

Further according to the present invention, a capacitive touch screen device is disclosed. The device includes a sensor layer having a plurality of capacitive sensors. A capacitance is created between the sensor layer and a body part of a user. The device also includes circuitry to determine a current that flows from the device to the body part through a bodily fluid placed on a layer of the device. The device also includes an analysis module to provide an indication of a medical condition based on the current. The analysis module compares a value of the bodily fluid determined from the current to a plurality of values corresponding to the medical condition.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

FIG. 4 illustrates a flowchart for using a measurement to diagnose a medical condition using the capacitive touch screen device according to the disclosed embodiments.

FIG. 5 illustrates a flowchart for analyzing the bodily fluid using the capacitive touch screen device according to the disclosed embodiments.

DETAILED DESCRIPTION OF THE PREFERRED EMBODIMENTS

Figure 1:
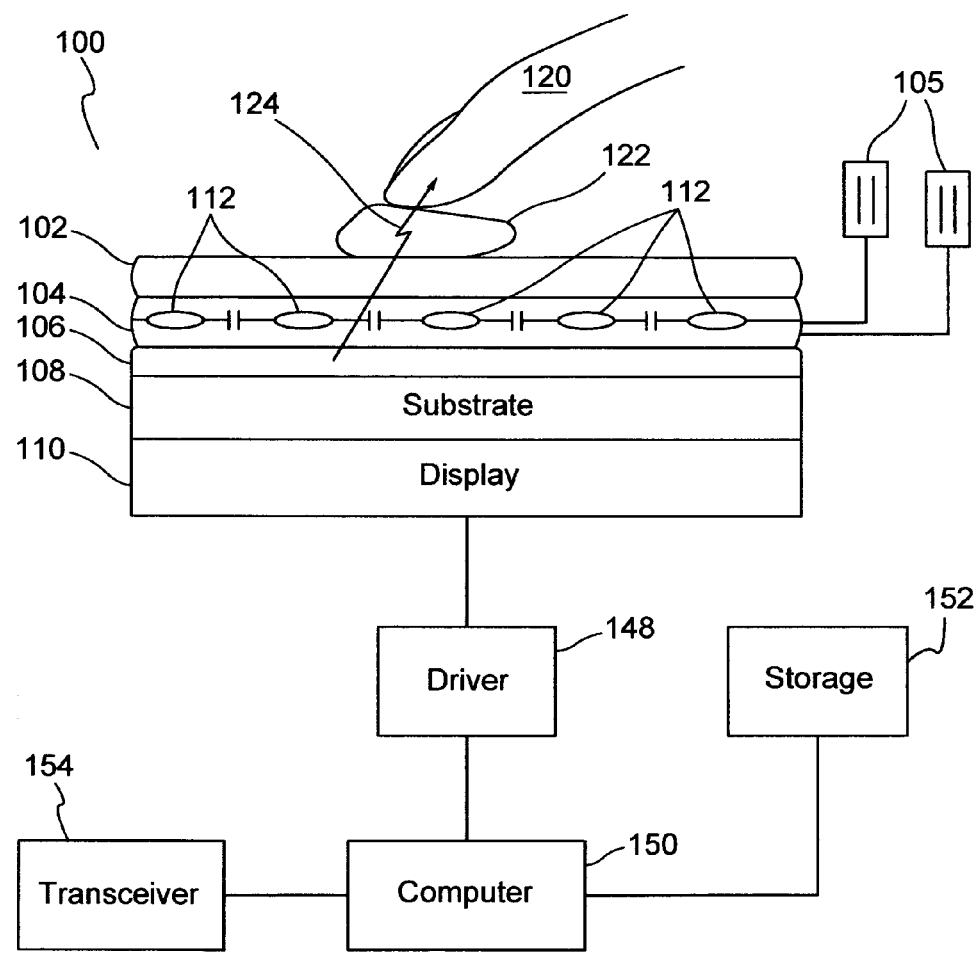
FIG. 1 illustrates a capacitive touch screen device for use in medical diagnosis according to the disclosed embodiments.

Aspects of the invention are disclosed in the accompanying description. Alternate embodiments of the present invention and their equivalents are devised without parting from the spirit or scope of the present invention. It should be noted that like elements disclosed below are indicated by like reference numbers in the drawings.

FIG. 1 depicts a capacitive touch screen device 100 for use in medical diagnosis according to the disclosed embodiments. Device 100 includes any device, apparatus or platform that incorporates a capacitive touch screen to receive and display information. For example, device 100 may be a personal digital assistant, a smart phone, a computer, a hand-held computer, a laptop computer, a tablet computer and the like. Device 100 also may be used in a kiosk or stand-alone machine that incorporates the disclosed embodiments for medical analysis or diagnosis. In other words, a user may utilize device 100 as long as a capacitive touch screen capability is enabled so that the user may press a finger to the touch screen.

Referring to FIG. 1, device 100 includes a capacitive touch screen configuration having various layers. The disclosed layers are exemplary, and device 100 may include additional layers. Alternatively, device 100 may not include all of the layers disclosed below.

The top layer of device 100 may be protective layer 102. Protective layer 102 may be clear and comprised of plastic, glass and the like. Protective layer 102 also serves to prevent scratches, dust, or other harm occurring to the other layers of device 100. Protective layer 102 also reduces glare from display 110, or off of the other layers disclosed below. Protective layer 102 also may limit the capacitive coupling between body part 120 and sensor layer 104. Thus, protective layer 102 may have a thickness proportional to a desired limit on the capacitive coupling. Moreover, protective layer 102 may be attached to the other layers by a user.

Device 100 also includes sensor layer 104. Sensor layer 104 may be a dielectric layer that includes capacitive sensors 112. Capacitive sensors 112 may be small plates embedded in sensor layer 104 that have a horizontal parasitic capacitance between each other, as disclosed in greater detail below.

As body part 120 approaches capacitive sensors 112, capacitances form between these elements that cause a current 124 to flow to body part 120. Body part 120 preferably is a finger or thumb of the user, but may be any part, such as a palm or forehead of the user. Any part of the human body may be used as body part 120. Some of the charge of sensor layer 104 is transferred to body part 120. Charge on sensor layer 104, in turn, decreases. The decrease in charge is measured by circuits 105, which may be located at the corners of sensor layer 104.

Plate layer 106 is attached to sensor layer 104 and establishes a vertical parasitic capacitance between itself and capacitive sensors 112. Plate layer 106 may provide a resistance feature to device 100 in order to generate current 124 through sensory layer 104. Thus, plate layer 106 may establish a capacitive coupling with body part 120 according to the disclosed embodiments.

Substrate layer 108 and display 110 also form the screen for device 100. Substrate layer 108 also preferably is clear. Display 110 provides visual information to the user and may direct the user where to touch device 100 with body part 120. Other layers may be incorporated into device 100 as needed, and known in the art. Circuits 105 relay information regarding current 124 and the decrease in charge to driver software 148. Other elements for this part of device 100 may include an oscillator to oscillate an electrical signal across sensor layer 104.

Device 100 also includes computer or processor 150, storage device 152 and transceiver 154. Computer 150 is disclosed in greater detail below. Storage device 152 is memory that allows retention of data or determinations compiled by computer 150. Transceiver 154 may exchange this information with another entity within a network. For example, if device 100 is a hand-held device, then transceiver 154 may receive authorization codes to enable device 100 and then forward the results generated to another computer. Storage device 152 and transceiver 154 may be common elements of any computer, smart phone and the like.

According to the disclosed embodiments, current 124 flows to body part 120 from device 100 through bodily fluid 122. Bodily fluid 122 may be sweat, blood, saliva and the like. Bodily fluid 122 includes electrolytes having a certain resistance to current 124. Device 100 uses this value to determine an estimated value for the concentration of electrolytes within bodily fluid 122. The estimated value corresponds with the possible amount of sodium chloride in bodily fluid 122. The value, in turn, may be used to diagnose or determine medical conditions for the user, such as cystic fibrosis, based on the possible amount of sodium chloride.

The following disclosure uses the cystic fibrosis example to explain features of the present invention, especially to determine the resistance of bodily fluid 122. Resistance relates to the conductivity of bodily fluid 122, and conductivity also may be used to determine the probability of cystic fibrosis. The disclosed embodiments, however, are not limited to the diagnosis of cystic fibrosis. Further, the amount of current 124 may be used to determine conductivity or impedance of bodily fluid 122 instead of the resistance.

Figure 2:
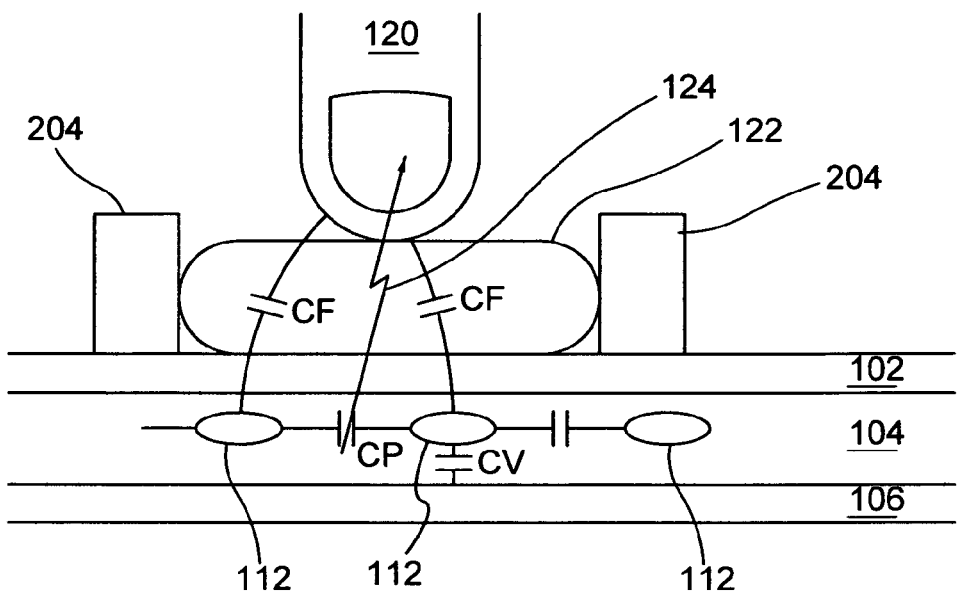
FIG. 2 illustrates the capacitive relationships between the capacitive sensors and other elements of the capacitive touch screen device according to the disclosed embodiments

FIG. 2 depicts the capacitances between capacitive sensors 112 and other elements of device 100 according to the disclosed embodiments. Bodily fluid 122 is shown as well. The disclosed embodiments use capacitive touch screen properties to conduct an electrical transfer from a human, or other living creature, to device 100. The transfer elicits current 124 to flow through bodily fluid 122. Disease states that alter conductivity may be diagnosed through sensing current 124 and resulting change in the charge within sensor layer 104.

Body part 120 creates a coupling capacitance, or $C_F$, with sensors 112. By being in close proximity to capacitance sensors 112, couple capacitances $C_F$ establishes enough capacitance to generate current 124 from device 100. Couple capacitances $C_F$ may be approximately equal. The capacitance between one sensor 112 to body part 120 and back to another sensor 112 adds in parallel to horizontal parasitic capacitance $C_P$ between the sensors to change the overall capacitance between the sensors.

Body part 120 may be connected to a "ground" to provide a path when it is close to or touching protective layer 102. The capacitive coupling relationship allows current 124 to flow from device 100. A relatively low impedance path to ground is provided for an oscillator signal, disclosed in greater detail below. When the capacitive coupling is formed, current 124 flows through device 100 to body part 120. An output voltage also may be produced correlating to current 124, as well as a reduction in the charge within sensor layer 104.

Capacitance sensors 112 are arranged in a matrix, such that sensor layer 104, as well as the other layers, is arranged in rectangular shape. Capacitance sensors 112 detect the presence of body part 120. Each sensor is assigned a predetermined area on the screen for device 100. Horizontal parasitic capacitance $C_p$ is generated using the oscillator signal coupled to the matrix of capacitance sensors 112. Capacitance $C_P$ may be a small edge-to-edge capacitance. Capacitance sensors 112 also may couple to circuits 105 to provide information on the location that is touched by body part 120.

Plate 106 serves to create a vertical parasitic capacitance $C_V$. Plate 106 may be an optional element of device 100. Sensor layer 104 may include dielectric material surrounding capacitance sensors 112. The material may be used to protect sensors 112 and to not bring them in contact with body part 120.

Device 100 also includes attachment 204. Attachment 204 may hold bodily fluid 122 in place on protective screen 102. For example, a user places sweat within attachment 204. Without attachment 204, the sweat may spill off device 100. Attachment 204 may be any shape, such as a circle, that allows for easy placement of bodily fluid 122. Further, attachment 204 may be removable to allow for cleaning or disposable use. Moreover, attachment 204 may be a specified size such that device 100 performs its analysis on a known or fixed amount of bodily fluid 122. This feature especially is important with regard to using blood as bodily fluid 122. Device 100 may require the user to fill attachment 204 before touching it, or drawing any current from device 100. Alternatively, attachment 204 may be placed on the back of device 100, or serve to send or receive a signal via device 100. For example, attachment 204 may be an electrode or the like to send or receive an electric signal from another attachment 204.

Bodily fluid 122 has certain parameters that may be measured by current 124 and the decrease in charge or output voltage created by the capacitive coupling between device 100 and body part 120. Using the cystic fibrosis example, a higher resistance may indicate a higher concentration of sodium chloride. Thus, a greater reduction of charge may indicate a possible condition such that the user should undergo further tests, if desired. Concentration of other chemicals, minerals or parts of bodily fluid 122 also may be determined by the resistance exhibited. These concentrations, as determined by the disclosed operations, indicate the probability of a variety of medical conditions.

Figure 3:
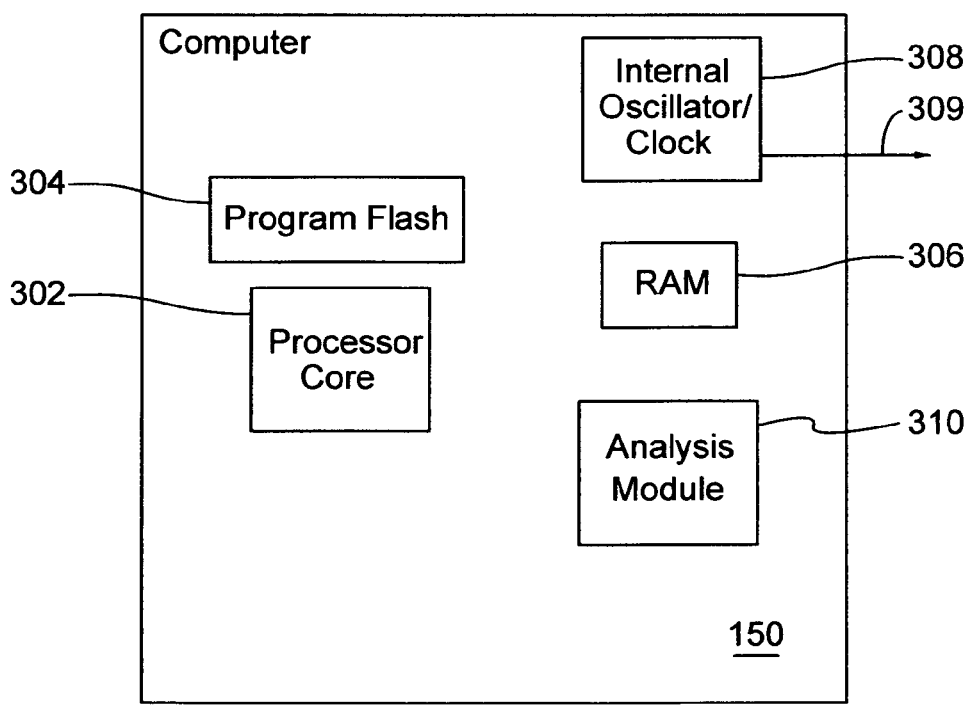
FIG. 3 illustrates a block diagram of a computer within the capacitive touch screen device according to the disclosed embodiments.

FIG. 3 depicts a block diagram of computer 150 within device 100 according to the disclosed embodiments. Computer 150 includes a processor core 302 that executes instructions, such as in a software program. Program flash memory 304 may be non-volatile storage used to store control algorithms executable by processor core 302. Computer 150 also includes random access memory (RAM) 306 for storage needs. Internal oscillator/clock 308 provides the clock signals for device 100 as well as a signal 309 to power capacitance sensors 112. This way, a separate signal is not generated and the disclosed embodiments may utilize a signal already available within device 100.

Computer 150 also may include analysis module 310. Analysis module 310 may be a program having a series of instructions that are executed by processor core 302. These instructions control device 100 to perform the steps needed to determine a possible medical condition using the conductance or impedance of bodily fluid 122. Analysis module 310 also may include stored values or ranges that indicate the possible medical conditions. The functionality of analysis module 310 is disclosed in greater detail below.

FIG. 4 depicts a flowchart for diagnosing a medical condition using device 100 according to the disclosed embodiments. The steps disclosed below may be executed on device 100 by computer 150. Where appropriate, the disclosure references elements depicted in FIGS. 1-3 for illustration and example. The disclosed embodiments, however, are not limited in executing the steps to the features shown above, and may include additional features known to those in the art.

Device 100 displays information to the user via display layer 110. Device 100 may prompt the user to provide information or select from a list of options. As a touch screen device, the user can enter information or selections via device 100.

Step 402 executes by the user selecting a medical condition for analysis. Using the example from above, the user may select "cystic fibrosis" as the medical condition for analysis. Alternatively, the user may not select any condition as device 100 may use a default setting as to which condition to analyze, or device 100 may take a general reading of bodily fluid 122 for comparison against a variety of possible medical conditions. The selected condition is used to retrieve the appropriate information to analyze bodily fluid 122, and to determine, if needed, the type of bodily fluid 122 for analysis.

Step 404 executes by adding attachment 204 to device 100. This step may be optional, as an attachment may not be used. The user may place attachment 204 onto device 100 in a designated location, or anyplace, against protective screen 102. Step 406 executes by selecting or requesting that the user provide bodily fluid 122 for analysis. Step 406 may indicate to the user what bodily fluid 122 is desired to analyze for the medical condition selected above. For example, if cystic fibrosis is selected in step 402, then device 100 requests that the user provide sweat as bodily fluid 122. Alternatively, the user may select the type of bodily fluid 122 from a list shown on display layer 110 or entered by the user.

Step 408 executes by obtaining bodily fluid 122. Many different ways exist for obtaining bodily fluid 122. Using the example above, the user may engage in activity that produces sweat. For blood, the user may prick their finger to provide an amount sufficient for analysis. Step 410 executes by placing bodily fluid 122 in attachment 204, or, alternatively, directly on device 100. For example, the user may place the sweat into attachment 204 located on device 100.

Step 412 executes by touching body part 120 to bodily fluid 122. The user should strive to keep bodily fluid 122 between body part 120 and device 100. Step 414 executes by creating a capacitance between body part 120 and sensor layer 104, as disclosed above. Step 416 executes by drawing current from device 100 to body part 120, as disclosed above. Using the cystic fibrosis example, body part 120 is a finger that touches sweat so that current 124 flows through the sweat into the finger. Another way of looking at this step is that charge is transferred from device 100 to body part 120. The charge built up by the capacitances between body part 120 and sensor layer 104 flow through bodily fluid 122.

Step 418 executes by performing an analysis based on the selected medical condition, the type of bodily fluid 122 and the values determined from the drawing of the current from device 100. This step is disclosed in greater detail by FIG. 5 below.

Step 420 executes by providing the results of the analysis or taking other actions by the values determined by the draw of current 124. This act may include displaying the results, alerts, messages and the like on device 100. Essentially, step 420 informs the user as to the outcome determined by device 100. Other actions may include providing a pop-up if a medical condition is detected, such as the possibility of cystic fibrosis. Actions also include storing the results in storage 152 of device 100 or in an external storage. Device 100 also may transmit the results to another computer or through a network. If an error occurred, then device 100 may request that the user perform the analysis again.

FIG. 5 depicts a flowchart for analyzing bodily fluid 122 using device 100 according to the disclosed embodiments. FIG. 5 may further disclose step 418 of FIG. 4. Step 502 executes by detecting current 124 flowing from device 100 to body part 120. This process is disclosed in greater detail above.

Step 504 executes by measuring the amount of current 124 that leaves device 100 or the amount of charge transferred during the touching process to body part 120. The measurements may be determined using circuits 105, as these elements determine these amounts to pinpoint the location of the touch. A larger amount of current 124 or charge transferred from device 100 may indicate absorption by bodily fluid 122.

Using the cystic fibrosis example, a greater amount of current 124 may be drawn from device 100 by the sweat exhibiting characteristics of cystic fibrosis. Within cystic fibrosis patients, the chloride channels in epithelial (skin) cells are dysfunctional. Thus, chlorine is not reabsorbed as well as in normal cells. This condition creates an accumulation of salt in the sweat. The salt acts as a bridge for electricity. The more salt there is, the more bridges there are. Thus, a greater absorption of electricity occurs within the sweat. This conductivity is related to the resistance of the sweat, as conductivity is inversely proportional to resistance.

Step 506 executes by determining a value for the resistance of bodily fluid 122. Alternatively, device 100 may calculate a conductivity or impedance value for bodily fluid 122 instead of a resistance value. The determinations may be made using standards electrical formulas, as device 100 may use a standard voltage across sensor layer 104. Using this voltage and the measured current, a resistance or impedance value may be determined for bodily fluid 122. Analysis module 310 may perform these determinations.

For example, a user with cystic fibrosis may exhibit sweat having a resistance of 16,000 to 20,000 ohms, and due to the higher number of electrolytes, about 50% more conductive than sweat from a user not having symptoms of cystic fibrosis. Thus, analysis module 310 will compare the measured values for resistance with stored ranges of values that indicate the possibility of cystic fibrosis.

Step 508 executes by retrieving ranges for the selected bodily fluid 122. For example, if the user selects sweat above, then analysis module 310 retrieves ranges for conditions detectable using sweat. Step 510 executes by retrieving ranges based on the selected medical condition of interest. Using the example, the user selects cystic fibrosis as the medical condition. Analysis module 310 retrieves those ranges from detecting cystic fibrosis in the selected bodily fluid 122. Alternatively, a variety of ranges can be placed at the disposal of analysis module 310 using these steps. In other words, impedance or conductivity values are compared against a number of ranges to determine any possible medical condition.

Step 512 executes by comparing the measured value or values against the range or ranges retrieved by analysis module 310. Analysis module 310 determines the range that the value or values fall within. That range then indicates the existence of a possible medical condition. Using the above example, if bodily fluid 122 has a resistance of 18,000 ohms, then the user may suffer from cystic fibrosis and should be alerted. If bodily fluid 122 has a resistance of 5,000 then the user may not have cystic fibrosis. Analysis module 310 may determine a plurality of values for bodily fluid 122 and compare these values against several ranges for different medical conditions, so that more than one medical condition can be determined.

A calibration technique also may be used to determine the high and low range values for the indication of a medical condition. The calibration technique may apply to repeated use by an individual. The resistance for a low ion solution may be determined along with the resistance of a high ion solution. The range is set for the individual this way, and the measured resistance is compared against these values to indicate if the measured value falls outside the acceptable range.

Step 514 executes by indicating the existence of a possible medical condition or conditions based on the comparison above. If the measured value or values fall within a range, then the possibility of that medical condition is noted and provided to the user. If the measured value or values do not fall within any critical ranges, then a normal medical condition may be identified. Using the values, device 100 diagnoses whether the potential medical condition is present in the user.

Using the cystic fibrosis example, a user activates a personal digital assistance, or a smartphone having a capacitive touch screen. The user selects the appropriate tests to be run and that he will use sweat as the bodily fluid. The user then places a bead of sweat in an attachment located on the screen of the device. The user touches his finger to the attachment and bead of sweat. Current is drawn into the finger from the screen. The smartphone determines the amount of current and calculates the resistance of the sweat. A pop-up on the screen tells the user whether he suffers from cystic fibrosis as the resistance fell within the critical range.

Other examples include using two touches to device 100, such as with the thumbs of the user, and measuring the current drawn through the user for medical analysis. Another example may be measuring the skin conductance of a user. In this embodiment, a bodily fluid may not be used but just the current drawn into the user is measured to indicate a skin conductance to diagnose conditions, such as schizophrenia or heart disease.

The disclosed embodiments also may diagnose or detect routine medical information for a user. The salt content of a bodily fluid may be determined using the values for impedance, conductivity or resistance. For example, an athlete may place their sweat on device 100 to determine whether she is properly hydrated or in danger of being dehydrated. A lower salt level may be detected and the user alerted to get fluids in their body.

It will be apparent to those skilled in the art that various modifications and variations can be made in the disclosed embodiments of the privacy card cover without departing from the spirit or scope of the invention. Thus, it is intended that the present invention covers the modifications and variations of the embodiments disclosed above provided that the modifications and variations come within the scope of any claims and their equivalents.

What is claimed is:

1. A method for determining a possible medical condition using a touch screen device, the method comprising:
   placing a bodily fluid on a layer of the device;
   contacting a body part with the bodily fluid;
   drawing a current from the device to the body part through the bodily fluid;
   measuring the current drawn from the device;
   performing an analysis on the bodily fluid based on a measurement corresponding to the current drawn from the device; and
   indicating whether a probability for a medical condition exists based on the analysis.

2. The method of claim 1, further comprising comparing the measurement to a range of values to indicate the probability of the medical condition.

3. The method of claim 1, further comprising selecting the medical condition for diagnosis.

4. The method of claim 1, further comprising adding an attachment to the layer of the device, wherein the attachment holds the bodily fluid.

5. The method of claim 1, further comprising creating a capacitance between the body and a sensor layer of the device to generate the current.

6. The method of claim 1, wherein the measurement corresponds to a resistance or conductivity value of the bodily fluid.

7. A method for determining a potential medical condition using a touch screen device, the method comprising:
   drawing a current from the device to a body part of a user through a bodily fluid;
   determining a value for the bodily fluid based on the current including determining a resistance or conductivity value of the bodily fluid;
   comparing the value to a range of values corresponding to a medical condition; and
   providing a result to the user regarding the medical condition.

8. The method of claim 7, wherein the providing step includes displaying the result of the device.

9. The method of claim 7, further comprising placing the bodily fluid on the device.

10. The method of claim 9, further comprising adding an attachment to the device to hold the bodily fluid.

11. The method of claim 7, further comprising selecting the medical condition for diagnosis.

12. The method of claim 11, further comprising retrieving the range of values according to the selected medical condition.

13. A capacitive touch screen device comprising:
   a sensor layer having a plurality of capacitive sensors, wherein a capacitance is created between the sensor layer and a body part of a user;
   circuitry to determine and measure a current that flows from the device to the body part through a bodily fluid placed on a layer of the device; and
   an analysis module to provide an indication of a medical condition based on the current, wherein the analysis module compares a value of the bodily fluid determined from the current to a plurality of values corresponding to the medical condition.

14. The device of claim 13, further comprising a memory to store the plurality of values.

15. The device of claim 13, further comprising an attachment to hold the bodily fluid.

16. The device of claim 13, further comprising a transceiver to transmit the indication of the medical condition.

17. The device of claim 13, wherein the device comprises a mobile device, a smartphone or a personal digital assistant.

18. The device of claim 13, wherein the device comprises a tablet computer.

* * * * *